United States Patent
Cao et al.

(10) Patent No.: US 11,875,205 B2
(45) Date of Patent: Jan. 16, 2024

(54) DATA MATCH CODING SYSTEM FOR ORTHODONTIC APPLIANCES

(71) Applicant: uLab Systems, Inc., Memphis, TN (US)

(72) Inventors: Henry Cao, San Jose, CA (US); Yongjie Zhang, Xi'an (CN); Lishun Tong, Xi'an (CN); Bo Zhu, Memphis, TN (US); Song Chen, Xi'an (CN)

(73) Assignee: uLab Systems, Inc., Memphis, TN (US)

( * ) Notice: Subject to any disclaimer, the term of this patent is extended or adjusted under 35 U.S.C. 154(b) by 0 days.

(21) Appl. No.: 18/067,138

(22) Filed: Dec. 16, 2022

(65) Prior Publication Data
US 2023/0214625 A1 Jul. 6, 2023

Related U.S. Application Data

(60) Provisional application No. 63/266,337, filed on Jan. 3, 2022.

(51) Int. Cl.
*G06K 19/06* (2006.01)
*A61C 7/08* (2006.01)

(52) U.S. Cl.
CPC .......... *G06K 19/06037* (2013.01); *A61C 7/08* (2013.01)

(58) Field of Classification Search
None
See application file for complete search history.

(56) References Cited

U.S. PATENT DOCUMENTS

| | | | |
|---|---|---|---|
| 6,976,627 B1 * | 12/2005 | Culp | B33Y 80/00 235/462.01 |
| 7,306,152 B2 | 12/2007 | Culp et al. | |
| 7,611,058 B2 | 11/2009 | Culp et al. | |
| 10,335,250 B2 | 7/2019 | Wen | |
| 10,357,336 B2 | 7/2019 | Wen | |
| 10,357,342 B2 | 7/2019 | Wen | |
| 10,548,690 B2 | 2/2020 | Wen | |
| 10,588,723 B2 | 3/2020 | Falkel | |
| 10,624,717 B2 | 4/2020 | Wen | |
| 10,624,722 B1 * | 4/2020 | Culp | B23K 26/38 |
| 10,631,953 B2 | 4/2020 | Wen | |
| 11,007,042 B2 * | 5/2021 | Long | B29C 64/20 |
| D942,015 S | 1/2022 | Hepler | |
| D974,566 S | 1/2023 | Tong et al. | |
| D975,284 S | 1/2023 | Tong et al. | |
| 2006/0093987 A1 | 5/2006 | Wen | |
| 2016/0128811 A1 | 5/2016 | Rauh et al. | |
| 2016/0338806 A1 | 11/2016 | Nazzal et al. | |
| 2017/0100208 A1 | 4/2017 | Wen | |

(Continued)

FOREIGN PATENT DOCUMENTS

| | | | | |
|---|---|---|---|---|
| CN | 114919180 A * | 8/2022 | ....... | G06K 19/06037 |
| WO | WO 2006/055239 | 5/2006 | | |

*Primary Examiner* — Kristy A Haupt
(74) *Attorney, Agent, or Firm* — Levine Bagade Han LLP

(57) ABSTRACT

Data match coding system for orthodontic appliances are disclosed. One variation of a data match code apparatus may generally comprise a three-dimensional model corresponding to a patient dentition and a platform extending from the three-dimensional model. The platform may define a data match code having a plurality of through-holes which are positioned relative to one another in a predetermined pattern.

17 Claims, 9 Drawing Sheets

(56) References Cited

U.S. PATENT DOCUMENTS

| | | |
|---|---|---|
| 2018/0078335 A1 | 3/2018 | Falkel |
| 2018/0078343 A1 | 3/2018 | Falkel |
| 2018/0078344 A1 | 3/2018 | Falkel |
| 2019/0321135 A1 | 10/2019 | Wen |
| 2019/0343602 A1 | 11/2019 | Wen |
| 2020/0146775 A1 | 5/2020 | Wen |
| 2020/0170762 A1 | 6/2020 | Falkel |
| 2020/0205936 A1 | 7/2020 | Wen |
| 2021/0045855 A1* | 2/2021 | Long ................ A61C 7/08 |

* cited by examiner

DATA MATCH CODING SYSTEM FOR ORTHODONTIC APPLIANCES

CROSS-REFERENCE TO RELATED APPLICATIONS

The present application claims the benefit of priority to U.S. Provisional Application 63/266,337 filed Jan. 3, 2022, which is incorporated herein by reference in its entirety.

FIELD OF THE INVENTION

The present invention relates to methods and apparatus for orthodontics. More particularly, the present invention relates to methods and apparatus for identifying or tracking orthodontic appliances during manufacturing of the appliances.

BACKGROUND OF THE INVENTION

In manufacturing some orthodontic appliances, particularly when large numbers of customized appliances are fabricated, identifying and/or tracking such appliances may be difficult. Bar codes such as one-dimensional bar codes are made of a coded pattern of indicia such as bars and spaces positioned adjacent to one another. Such one-dimensional bar codes reflect light through which electro-optical scanners detect the reflected characteristics to produce a unique set of alphanumerical characters which are used to identify a particular item associated with the bar code.

However, one-dimensional bar codes are limited in the amount of information which can be conveyed within a particular given area.

Other two-dimensional bar codes such as Quick Response (QR) codes are generally comprised of a two-dimensional matrix which allows for the encoding of more information in a two-dimensional pattern within a smaller area. Such codes typically include black squares which are arranged in a square grid on a white background and are read by an imaging device such as a camera.

Like the one-dimensional bar code, the imager receives light reflected from the two-dimensional bar code but may not be suitable for mass fabrication of items.

Yet another identification mechanism includes three-dimensional (3D) bar codes which utilize marks which are created to utilize their 3D relief in order to determine where the bars and spaces reside. Capturing a 3D bar code typically uses a light source such as a laser and an imager which is offset from the light source in order to detect the relative differences in relief in the 3D bar code.

Yet the creation of the 3D bar code requires the use of stereolithography to fabricate the 3D bar code and also requires the use of equipment for detecting the 3D bar code and thus may not be suitable for the rapid detection and tracking of multiple items.

Accordingly, a system which allows for the tracking and identification of multiple items using an identification mechanism which allows for greater information storage in a limited space with the automated fabrication and handling of items and rapid detection is desired.

SUMMARY OF THE INVENTION

In treating a patient for one or more malocclusions in the positioning of their teeth, one or more corresponding aligners may be formed for treating the patient. However, multiple aligners and multiple patients may require the tracking and maintenance of a particular aligner or other orthodontic appliance. In order to establish a correspondence between a particular patient and their associated oral appliance, one or more three-dimensional tooth models which are representative of the patient's dentition and used in treatment planning for correcting the positioning of their teeth may be associated with the patient. The three-dimensional tooth models may be printed, e.g., by photosensitive resins, and various information such as patient information, aligner information, trimming information, etc. which can be associated with that particular three-dimensional tooth model may be integrated directly with the tooth model. For example, the trimming machine may be programmed to automatically call the cutting curve function for cutting or trimming an aligner from the tooth model based on the information encoded upon or into the tooth model itself.

The information which may be encoded may comprise a data match code which can be directly printed or otherwise integrated upon the tooth model and this data match code can be imaged and used for information transmission. Since the tooth model may incorporate the data match code information, an imager and machine vision can be implemented to recognize the data match code to automatically capture and transmit this information.

Three-dimensional dentition models may be fabricated such as by a three-dimensional printing process using, e.g., photosensitive resins, and various information such as patient information, aligner information, trimming information, etc. which can be associated with that particular three-dimensional dentition model may be integrated directly with the dentition model. The information which may be encoded may comprise a data match code which can be directly printed or otherwise integrated upon the dentition model at a fixed location on the three-dimensional dentition model.

The three-dimensional dentition model and data match code may be positioned and aligned upon a plate platform and a corresponding aligner or other orthodontic appliance may be formed by a polymeric film layer, such as by a thermoforming process, directly upon the three-dimensional tooth model and data match code. As the thermoformed aligner and film layer formed upon the data match code remain translucent, an image of the data match code upon the tooth model may be captured through the film layer via an imager.

The image of the data match code can be captured and processed to convert the data match code into identifying information, such as an alphanumeric code, which may be used for information transmission. The information may be used as a unique identifying code for associating with a particular patient and/or the information may also be used for providing instructions, for instance, for tracking, processing, etc. In one example, the trimming machine may be programmed to automatically call the cutting curve function for cutting or trimming an aligner from the dentition model based on the information encoded upon or into the dentition model itself.

The dentition model may incorporate an integrated platform which may be positioned within the arch of the dentition where the platform provides a surface for displaying the data match code which may comprise an information code formed of multiple through-holes which are positioned at predetermined positions relative to one another and which extend through the entirety of the platform. A reference hole may be formed at a specified location upon the platform relative to the placement of the through-holes such that the reference hole is fixed at the same location between each of the different dentition models. With the reference hole position fixed, the through-holes of the data match code may be formed at a consistent location relative to the reference hole upon the platform so that locating and identifying the data match code during imaging is facilitated. When the data match code is imaged, the location of the reference hole may provide a constant location for determining the relative positioning of the data match code image for consistency purposes between different dentition models. While each data match code may be different and unique to a particular dentition model and patient resulting in individual through-holes being located at different positions and spaces relative to one another, the entirety of the data match code relative to the reference hole may be consistent between different models.

With the dentition model and unique data match code fabricated, the dentition model may be positioned upon a surface of a positioning plate such that the positioning splines are aligned to one or more positioning features on the positioning plate. With the dentition model desirably positioned upon the positioning plate, a polymeric film or membrane used to form an aligner may be formed upon the dentition model using any number of various processes such as thermoforming or heat-pressing. As the film or membrane is transparent or at least translucent, the data match code located upon the platform may still be visible through the film or membrane.

Generally, an image of the data match code may be captured by an imaging system which may illuminate a light source to transmit a light either from a top or bottom of the platform and through the data match code for capturing the resulting image. This captured image may be processed, e.g., by a processor connected to the image capture system, in order to convert the image into a corresponding black-and-white image which may then be reconstructed into a gray value image. This gray value image may then be converted via the processor into a corresponding numeric value such as an alpha-numeric value which may correspond to a unique identifier associated with a particular patient and/or to a set of instructions unique to the orthodontic appliance being fabricated, such as numerical machine instructions. This value may also be associated with any number of instructions or identifiers as desired and is not limited.

The patterned image formed by the through-holes of the data match code when a back light transmitted from a light source is transmitted through a platform. The imaged data match coding as received from the imager may be recognized by the processor so that the imaged data match coding with gray-value image features may reconstruct the data match codes with gray-value image features. Hence, the imaged data match coding may be converted into a black-and-white image where the light transmitted through a through-hole is converted into a white-colored square and spaces or locations between or adjacent to the through-hole where the light is blocked is converted into a black-colored square. The resulting black-and-white image may correspond to a digitized version corresponding to the imaged data match coding.

The black-and-white image may then be processed by the processor for conversion into a recognized alphanumeric value. Multiple data match codes from different orthodontic appliances may be imaged sequentially by the imaging system and the images may be stored in a memory component and sent to the processor for analysis and processing.

One variation of a data match code apparatus generally comprises a three-dimensional model corresponding to a patient dentition and a platform extending from the three-dimensional model, wherein the platform defines a data match code having a plurality of through-holes which are positioned relative to one another in a predetermined pattern.

Another variation of a data match code apparatus generally comprises a three-dimensional model corresponding to a patient dentition, a platform extending from the three-dimensional model, wherein the platform defines a data match code having a plurality of through-holes which are positioned relative to one another in a predetermined pattern, a film or membrane formed upon the three-dimensional model and the platform such that the data match code is visible through the film or membrane, and an imager configured to be in alignment with the data match code such that the imager receives an image of the predetermined pattern when a light is transmitted through the through-holes from a bottom or top surface of the platform.

One variation of a method of coding an oral appliance generally comprises exposing a light upon a bottom or top surface of a platform which defines a data match code having a plurality of through-holes which are positioned relative to one another in a predetermined pattern, where the platform extends from a three-dimensional model which corresponds to a patient dentition, receiving an image upon an imager in communication with a processor, where the image is formed by a portion of the light transmitted through the plurality of through-holes to form the image which corresponds to the predetermined pattern, converting via the processor the image to a composite image, and converting via the processor the composite image to an alphanumeric value which corresponds to a unique identifier associated with the oral appliance.

DETAILED DESCRIPTION OF THE INVENTION

With treatment planning software, a treatment plan using aligners, brackets, etc. may be used to correct for any number of malocclusions with a patient's teeth. Particular treatment planning processes are described in further detail in U.S. Pat. Nos. 10,624,717; 10,335,250; 10,631,953; 10,357,336; 10,357,342; 10,588,723; 10,548,690, as well as U.S. Pat. Pubs. 2017/0100208; 2019/0321135; 2020/0205936; 2019/0343602; 2020/0170762; 2018/0078343; 2018/0078344; 2018/0078335; 2020/0146775. The details of these references are incorporated herein by reference in their entirety and for any purpose.

As part of the treatment planning, a three-dimensional (3D) digital scan of the patient's dental arch prior to treatment is typically obtained using any number of scanning methodologies and processes. This 3D scan of the dental arch may be used to generate an electronic 3D digital model corresponding to the scanned dentition of the patient. It is this 3D digital model which may be digitally manipulated via a processor or controller within a processing device such as a computer, tablet, etc. for developing a treatment plan upon which one or more orthodontic aligners may be configured for fabrication.

Figure 1:
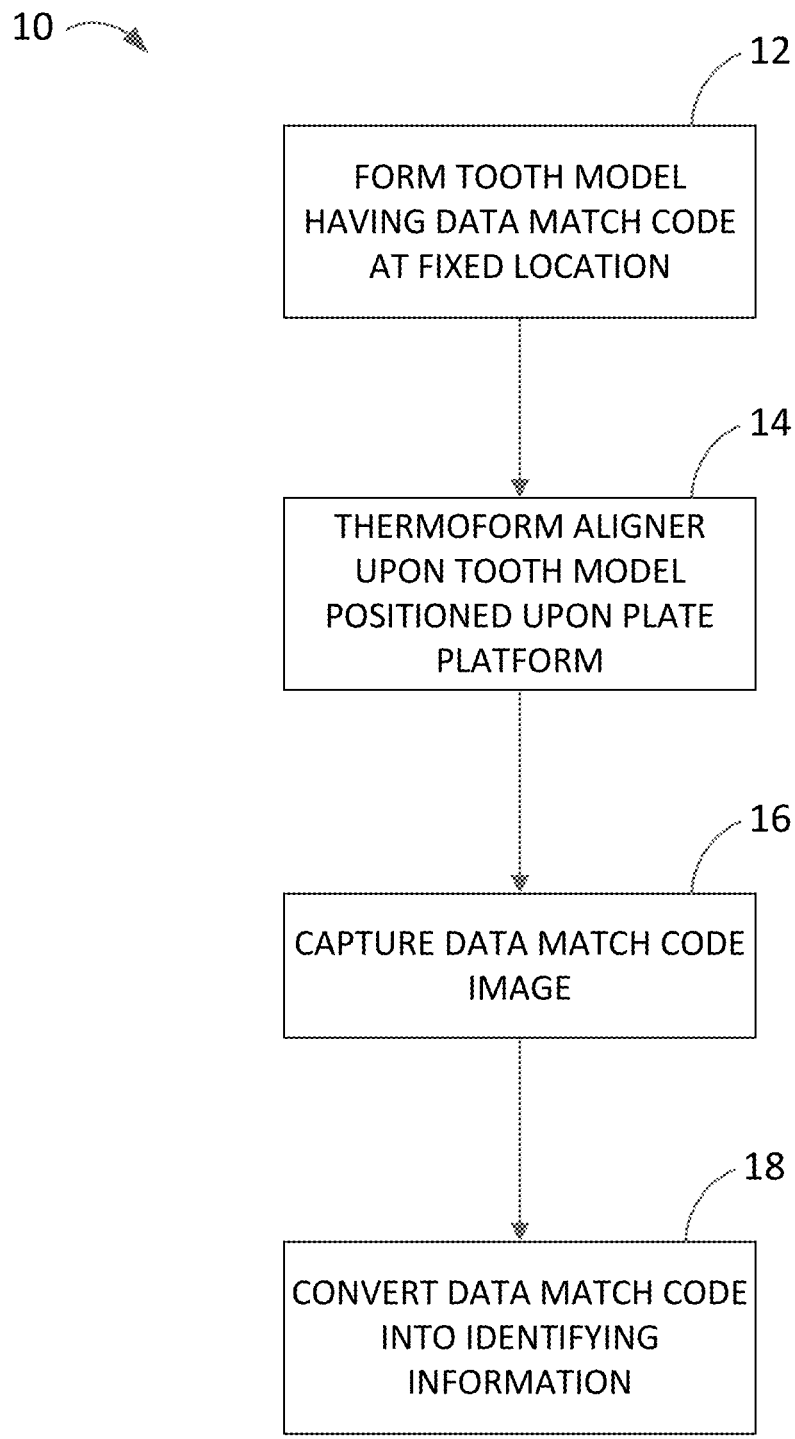
FIG. 1 illustrates a flow diagram of one variation of a method for capturing data using a data match coding system.

Generally, in order to establish a correspondence between a particular patient and their associated oral appliance, one or more three-dimensional dentition models based on scanned patient dentition may used in treatment planning for correcting the positioning of their teeth may be associated with the patient using the treatment planning software described above. With the scanned patient dentition data, FIG. 1 illustrates a flow diagram 10 generally showing one variation for integrating and utilizing a data match code system, as described herein.

The three-dimensional dentition models may be fabricated such as by a three-dimensional printing process using, e.g., photosensitive resins, and various information such as patient information, aligner information, trimming information, etc. which can be associated with that particular three-dimensional dentition model may be integrated directly with the dentition model. The information which may be encoded may comprise a data match code which can be directly printed or otherwise integrated upon the dentition model at a fixed location on the three-dimensional dentition model 12.

The three-dimensional dentition model and data match code may be positioned and aligned upon a plate platform and a corresponding aligner or other orthodontic appliance may be formed by a polymeric film layer, such as by a thermoforming process, directly upon the three-dimensional tooth model and data match code 14. As the thermoformed aligner and film layer formed upon the data match code remain translucent, an image of the data match code upon the tooth model may be captured through the film layer 16 via an imager.

The image of the data match code can be captured and processed to convert the data match code into identifying information, such as an alphanumeric code, which may be used for information transmission 18. The information may be used as a unique identifying code for associating with a particular patient and/or the information may also be used for providing instructions, for instance, for tracking, processing, etc. In one example, the trimming machine may be programmed to automatically call the cutting curve function for cutting or trimming an aligner from the dentition model based on the information encoded upon or into the dentition model itself.

Figure 2A:
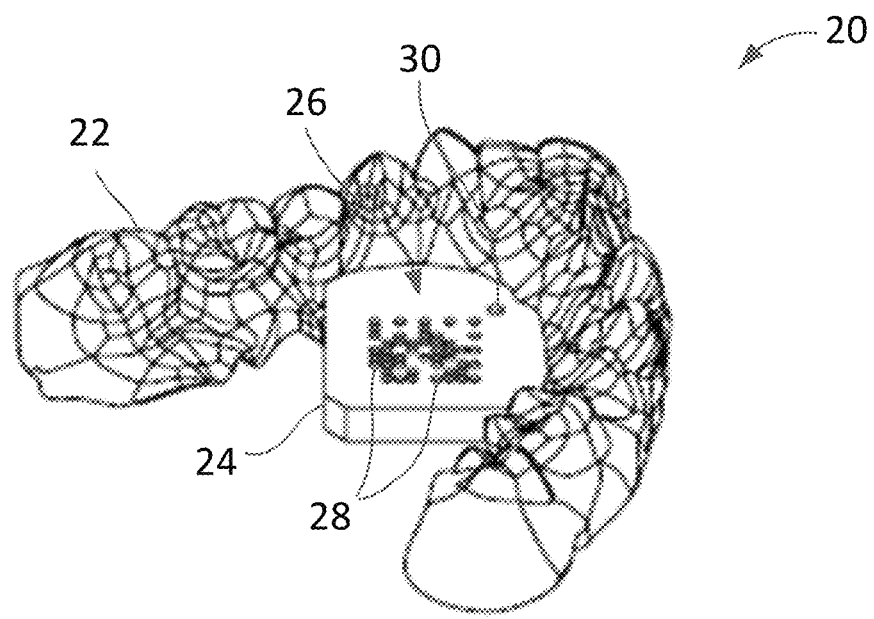
FIGS. 2A and 2B illustrate perspective views of an exemplary dentition model used for fabricating a corresponding aligner and having an integrated platform for implementing a data match code used for identifying and/or tracking the model.
Figure 2B:
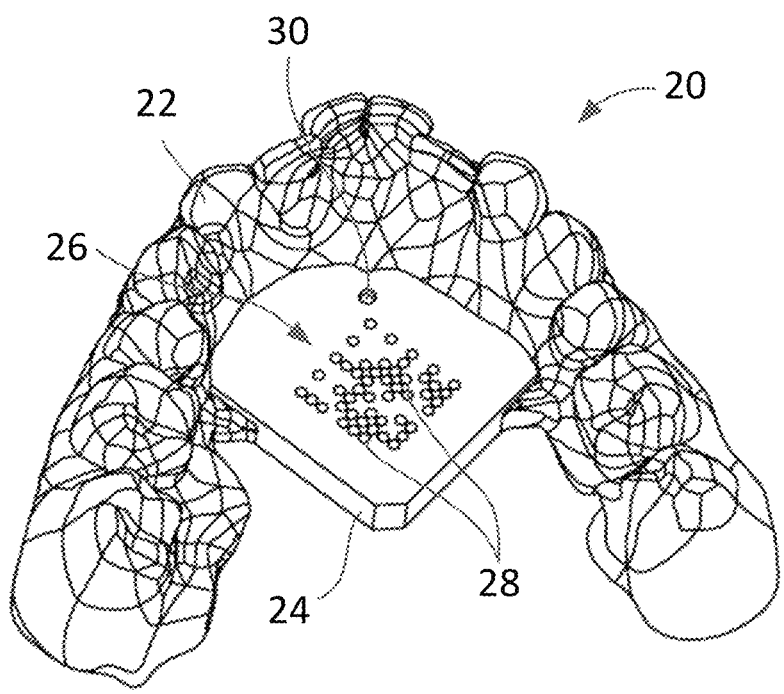

FIGS. 2A and 2B illustrate various perspective views perspective views of an exemplary three-dimensional dentition model 20 used for fabricating a corresponding aligner. The dentition model 20 may include the three-dimensional representation of the patient's dentition 22 based upon the scanned image data. The dentition model 20 may incorporate an integrated platform 24 which may be positioned within the arch of the dentition 22 where the platform 24 provides a surface for displaying the data match code 26 which may comprise an information code formed of multiple through-holes 28 which are positioned at predetermined positions relative to one another and which extend through the entirety of the platform 24. A reference hole 30 may be formed at a specified location upon the platform 24 relative to the placement of the through-holes 28 such that the reference hole 30 is fixed at the same location between each of the different dentition models 20. With the reference hole 30 position fixed, the through-holes 28 of the data match code 26 may be formed at a consistent location relative to the reference hole 30 upon the platform 24 so that locating and identifying the data match code 26 during imaging is facilitated. When the data match code 26 is imaged, the location of the reference hole 30 may provide a constant location for determining the relative positioning of the data match code image for consistency purposes between different dentition models. While each data match code 26 may be different and unique to a particular dentition model 20 and patient resulting in individual through-holes 28 being located at different positions and spaces relative to one another, the entirety of the data match code 26 relative to the reference hole 30 may be consistent between different models 20.

Figures 3A, 3B:
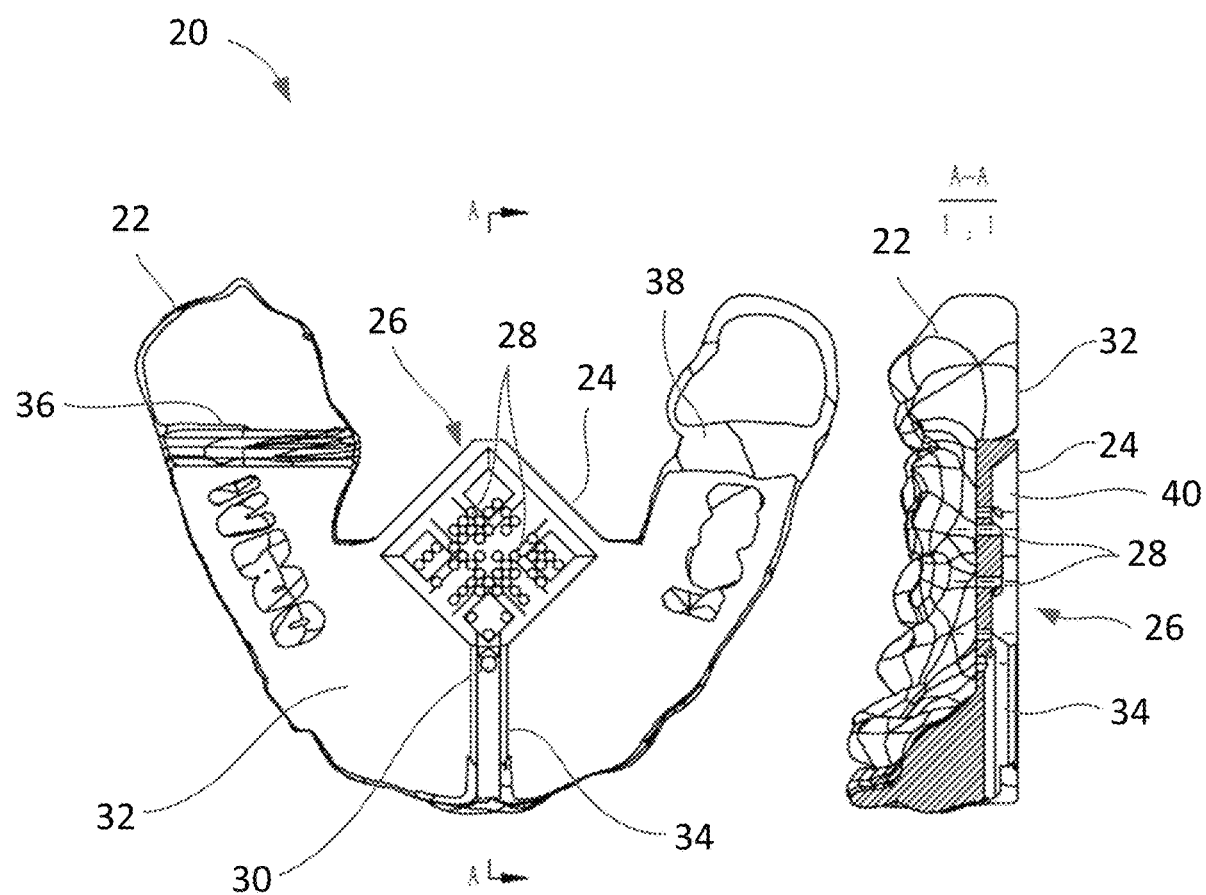
FIGS. 3A and 3B illustrate respective bottom and cross-sectional side views of the exemplary dentition model and data match code.

FIGS. 3A and 3B illustrate respective bottom and cross-sectional side views of the exemplary dentition model 20 and data match code 26. As shown, the various through-holes 28 forming the data match code 26 upon the platform 24 may be seen extending through the thickness of the platform 24. The platform 24 itself may define a cavity 40 such that the amount of material used for forming the platform 24 is reduced and the through-holes 28 need only extend through a reduced material thickness.

Additionally, the dentition model 20 may be formed with a flattened surface 32 which may further define one or more positioning splines. The first positioning spline 34 is shown extending longitudinally along a midline of the dentition model 20 and a second positioning spline 36 and a third positioning spline 38 may each extend transversely along the dentition model 20 in a lingual-buccal direction such that each of the positioning splines 34, 36, 38 are keyed to a corresponding positioning feature on a positioning plate for image capture, as described in further detail below.

With the dentition model 20 and unique data match code 26 fabricated, the dentition model 20 may be positioned upon a surface of a positioning plate 52 such that the positioning splines 34, 36, 38 are aligned to one or more positioning features 56, 58, 60, 62 on the positioning plate 52. In the example shown, the positioning splines 34, 36, 38 are aligned to the positioning features 56, 58, 60. Doing so ensures that the dentition model 20 is oriented in a consistent position between each of the different dentition models when placed upon the positioning plate 52.

Figure 4A:
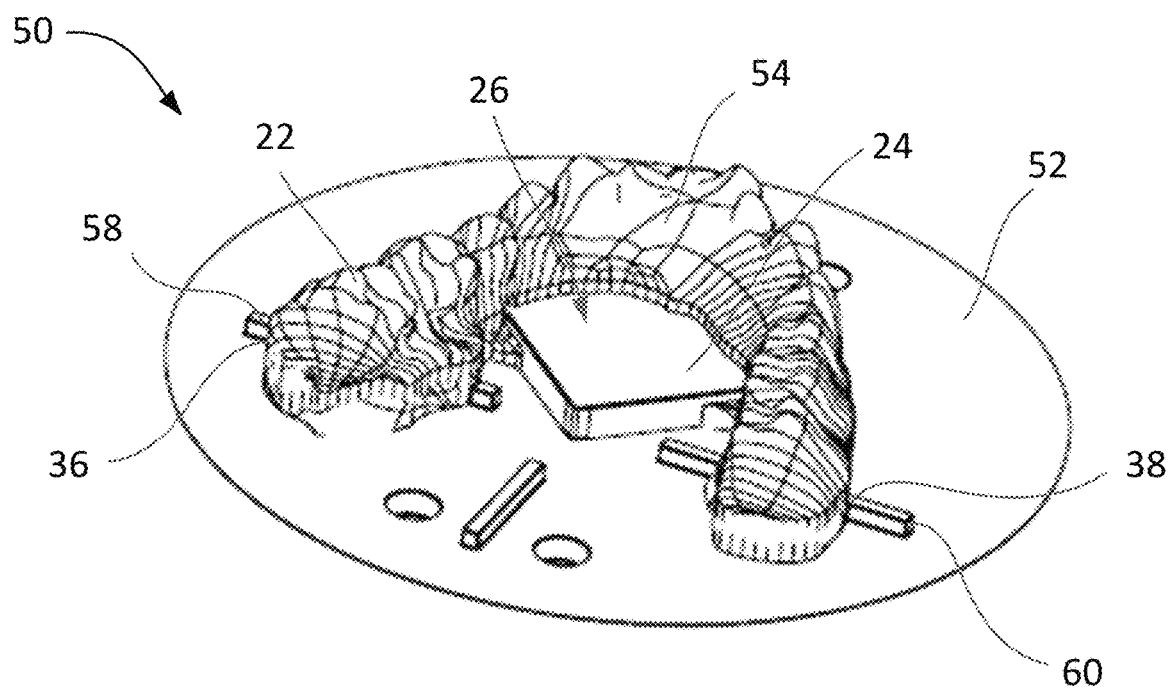
FIGS. 4A and 4B illustrate perspective views of the dentition model placed upon a positioning plate and having a thermoformed sheet formed upon the dentition model.
Figure 4B:
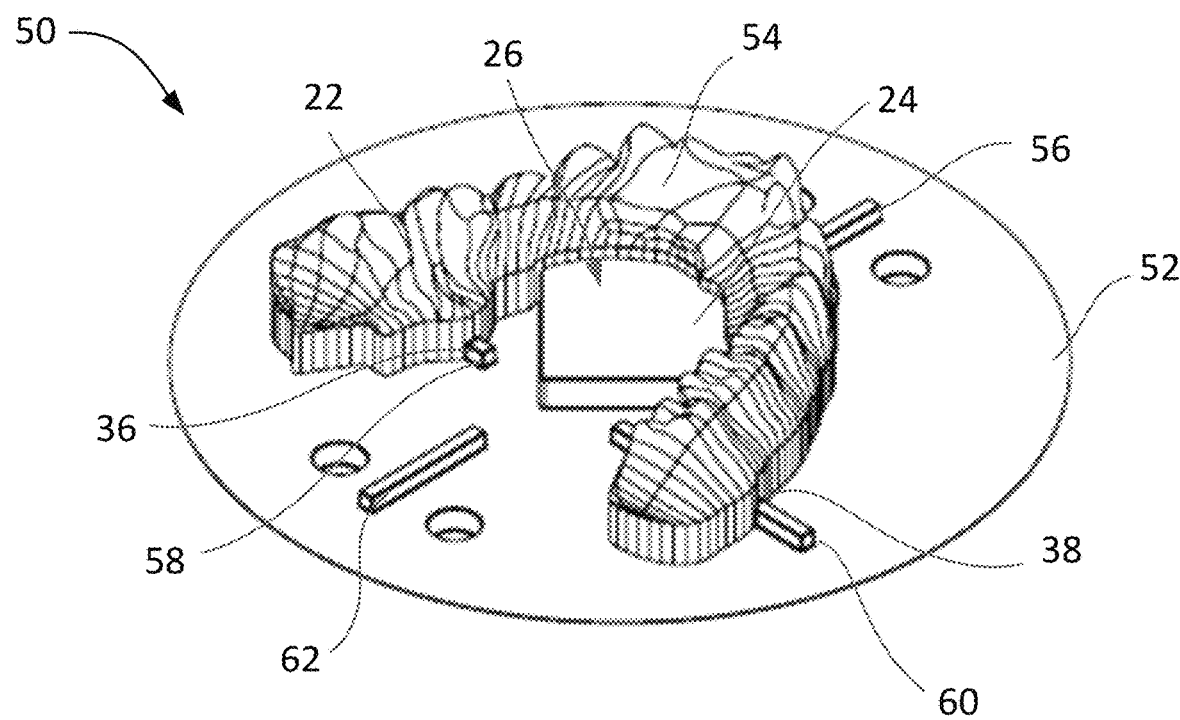

With the dentition model 20 desirably positioned upon the positioning plate 52, a polymeric film or membrane 54 used to form an aligner may be formed upon the dentition model 20 using any number of various processes such as thermoforming or heat-pressing. FIGS. 4A and 4B illustrate various perspective views of the film or membrane 54 thermoformed upon the dentition model 22, platform 24 and data match code 26, and the surface of the positioning plate 52 to form an assembly 50. As the film or membrane 54 is transparent or at least translucent, the data match code 26 located upon the platform 24 may still be visible through the film or membrane 54.

Figure 5A:
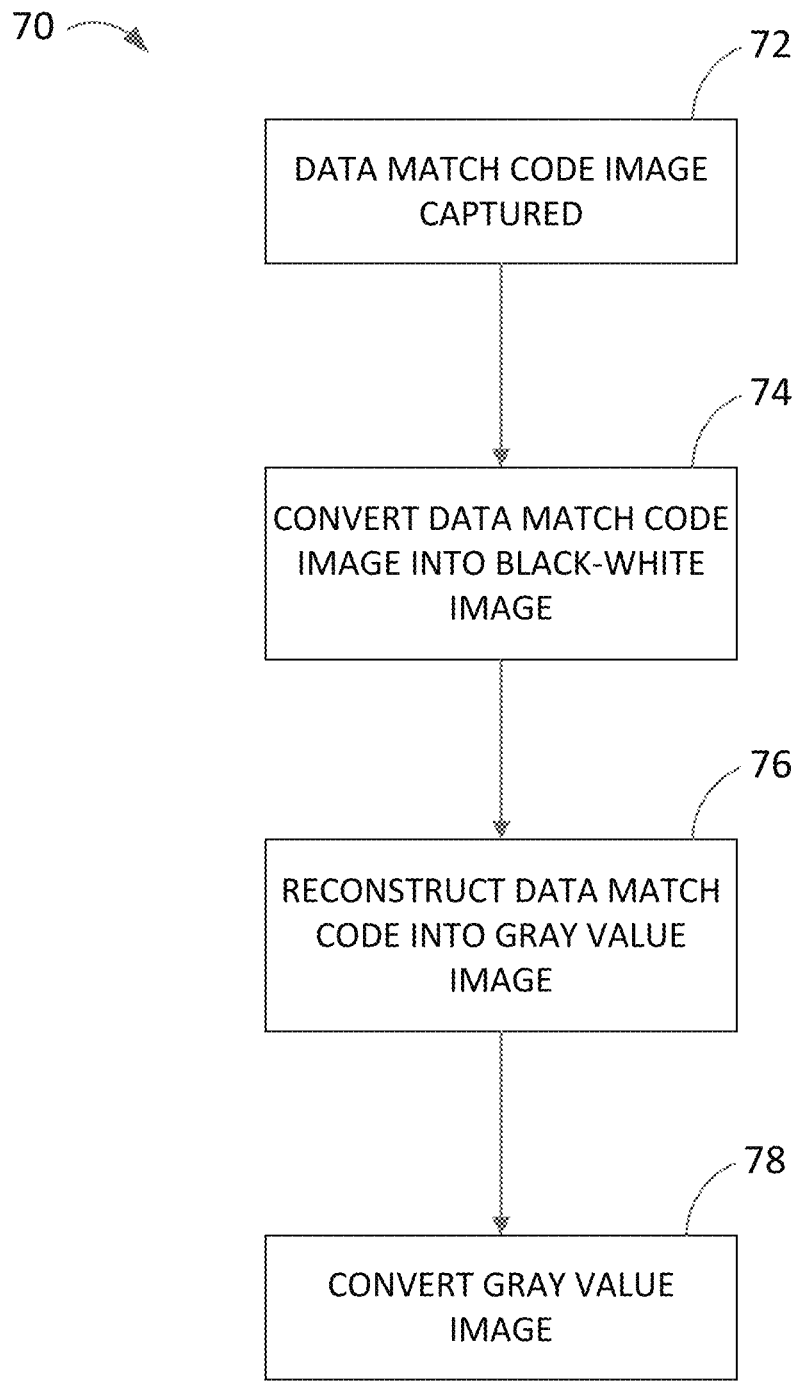
FIGS. 5A and 5B illustrate flow diagrams of variations of methods for converting the data match code to an image which can be converted into an alphanumeric value.

FIG. 5A illustrates a flow diagram 70 of one variation of a method for converting the data match code 26 to an image which can be converted into an alphanumeric value. Generally, an image of the data match code 26 may be captured 72 by an imaging system which may illuminate a light source to transmit a light through the data match code 26 for capturing the resulting image. This captured image may be processed, e.g., by a processor connected to the image capture system, in order to convert the image into a corresponding black-and-white image 74 which may then be reconstructed into a gray value image 76. This gray value image 76 may then be converted via the processor into a corresponding numeric value such as an alpha-numeric value 78 which may correspond to a unique identifier associated with a particular patient and/or to a set of instructions unique to the orthodontic appliance being fabricated, such as numerical machine instructions. This value 78 may also be associated with any number of instructions or identifiers as desired and is not limited.

Figure 5B:
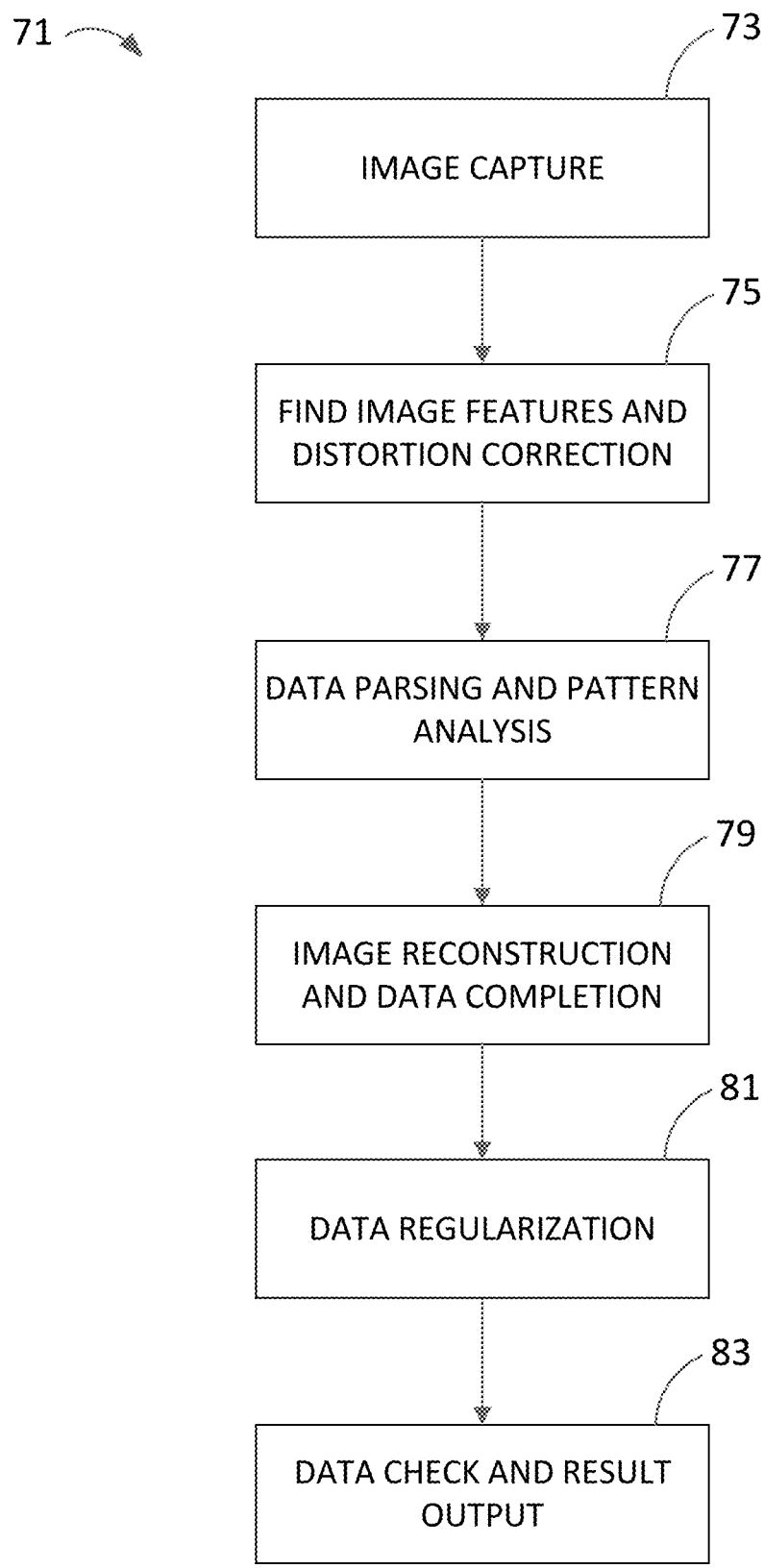

FIG. 5B illustrates a flow diagram 71 of another method for converting the data match code 26 to an image which can be converted into an alphanumeric value. Once the image has been captured 73 (using any of the processes and devices described), the individual image features may be determined by the processor 100 and any distortions in the image may be corrected 75 using a variety of image correction mechanisms. The captured data may be parsed and the pattern may be analyzed 77 by the processor 100. The image data may be reconstructed and the data completed 79 and subsequently regularized 81. The resulting image data may be checked and the result output 83.

Figure 6A:
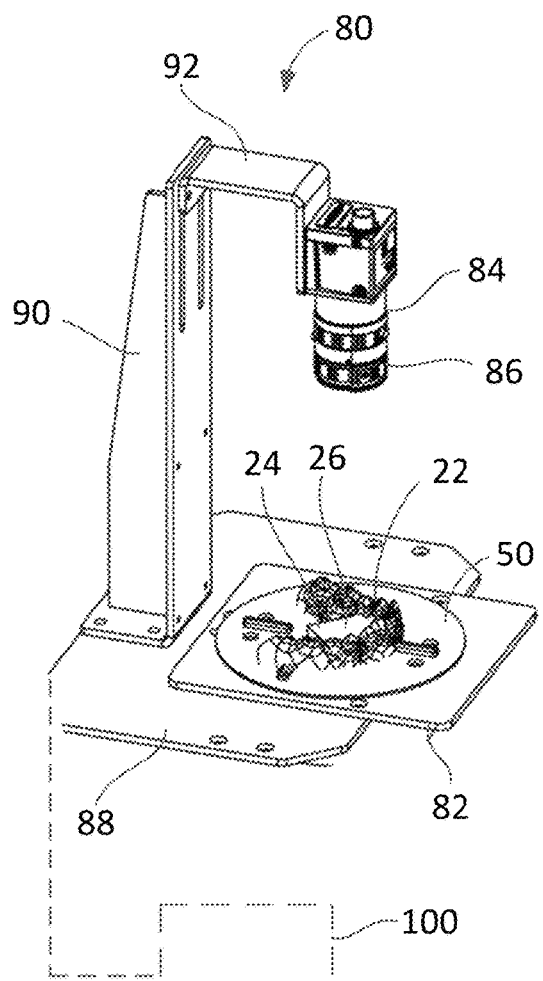
FIGS. 6A and 6B illustrate perspective assembly and expanded assembly views of an imaging system which may be used for imaging the data match coding.
Figure 6B:
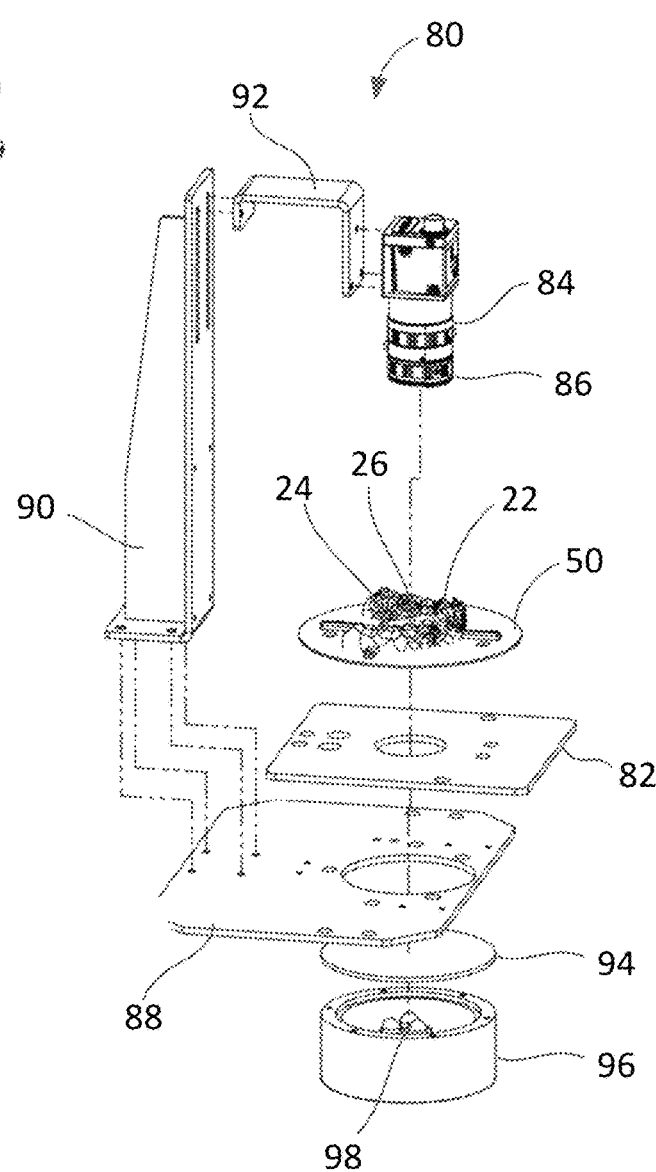

FIGS. 6A and 6B illustrate perspective assembly and expanded assembly views of an imaging system 80 which may be used for imaging the data match coding for processing via the processor 100 which may be electrically coupled (wired or wirelessly) to the imaging system. The assembly 50, including the positioning plate 52 with film or membrane 54 having the dentition model 22 and data match code 26 located upon the platform 24, may be positioned upon a positioning plate 82 in a predetermined orientation upon a base 88 of the imaging system 80. An imager 84, such as a CMOS camera (with or without zoom capability) having a camera lens 86, may be positioned upon a bracket or support 92 which extends from a main support 90 secured to the base 88 such that the imager 84 is positioned to extend over the assembly 50. The imager 84 may be aligned with the base 88 such that when the positioning plate 82 with the assembly 50 is placed upon the base 88, the imager 84 may be automatically aligned with the data match code 26 for imaging and transferring the captured image to the processor 100.

A light source 98 such as an infrared or white light source (or other light source) may be positioned within a housing 96 below the base 88 such that the light may be transmitted from the light source 98 and through an optional homogenizer or diffuser 94 which may be used to ensure uniformity of the transmitted light. The light source 98 may also be electrically coupled to the processor 100 as well. The homogenizer or diffuser 94 may be positioned above the light source 98 such that the transmitted light may pass through the homogenizer or diffuser 94 and through an opening defined within the base 88 to illuminate the bottom of the platform 24. The light may pass through the through-holes 28 defined within the platform 24 and through the film or membrane 54 while the remaining light is blocked by the remainder of the platform 24 such that the data match pattern formed by the through-holes 28 may be detected by the imager 84.

Figure 7A:
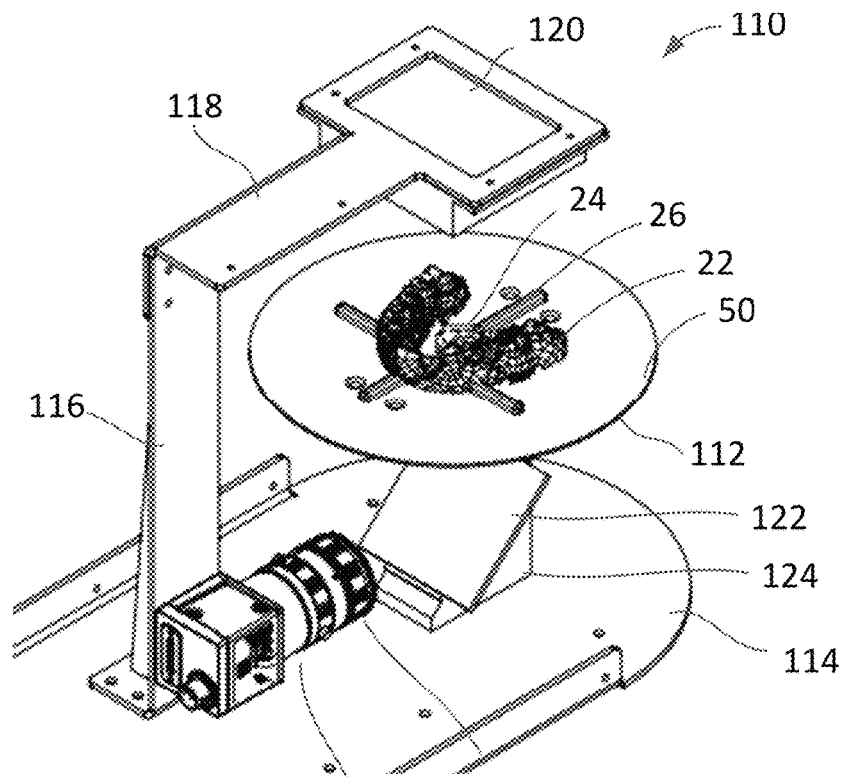
FIGS. 7A and 7B illustrate various perspective views of another variation of the imaging system which may be used for imaging the data match coding for processing.
Figure 7B:
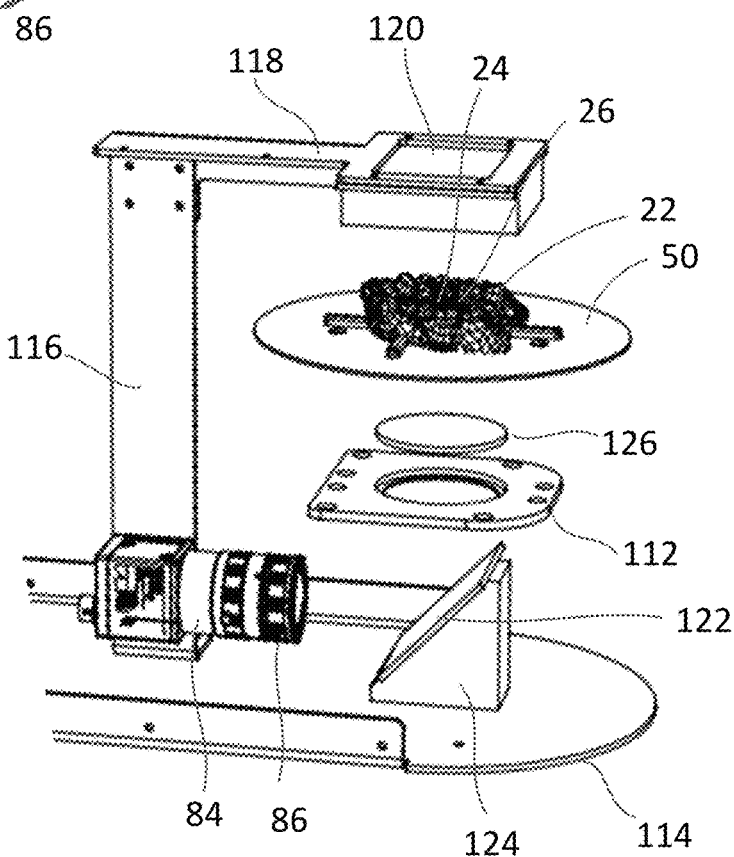

FIGS. 7A and 7B illustrate various perspective views of another variation of an imaging system 110 which may be used for imaging the data match coding for processing. The assembly 50 may similarly include a positioning plate 112 with the film or membrane having the dentition model 22 and data match code 26 located upon the platform 24, positioned upon a positioning plate 112 in a predetermined orientation relative to a base 114 of the imaging system 110. The imager 84, such as a CMOS camera (with or without zoom capability) having the camera lens 86, may be positioned upon the base 114 such that the imager 84 is pointed in parallel within the base 114 and the field of view is positioned below a position of the assembly 50. The light source 120 (e.g., infrared or white light source or other light source) may be supported upon a bracket or support 118 which extends from a main support 116 secured to the base 114, as shown, such that the light source 120 transmits its light below in a direction towards the surface of the base 114.

A mirror 122 positioned upon a support 124 which secured to the base 114 may have an angled support surface such that the mirror 122 is mounted upon the support surface at an angle (e.g., 45 degrees) relative to the surface of the base 114 and aligned relative to the imager 84. The mirror 122 may be positioned at other angles relative to the surface of base 114 so long as the imager 84 remains in alignment with the mirror 122. The light source 120 may be aligned with the support 124 and mirror 122 so that when the light source 120 emits its light, the light may be transmitted to the mirror 122 which may reflect the light at the angle and directly into the imager 84 for capture. The positioning plate 112 with the assembly 50 may accordingly be positioned directly within the path of the light so that the dentition model 22 and data match code 26 located upon the platform 24 is positioned into alignment with the light source 120 and mirror 122 which is also aligned at an angle with the imager 84 for imaging and transferring the captured image to the processor 100. An optional homogenizer or diffuser 126 may be positioned within the light path, e.g., with the positioning plate 112 which may define an opening for allowing the transmitted light to pass through. The homogenizer or diffuser 126 may be used to ensure uniformity of the transmitted light. The light source 120 may also be electrically coupled to the processor 100 as well.

As the light passes through the through-holes 28 defined within the platform 24 and through the film or membrane 54 while the remaining light is blocked by the remainder of the platform 24 such that the data match pattern formed by the through-holes 28 may be detected by the imager 84. The variation shown may facilitate the image capture by the imager 84 by allowing for a relatively cleaner imaging effect as the transmitted light from the light source 120 is transmitted through the top of the aligner sheet and down through the through-holes 28.

Figure 8A:
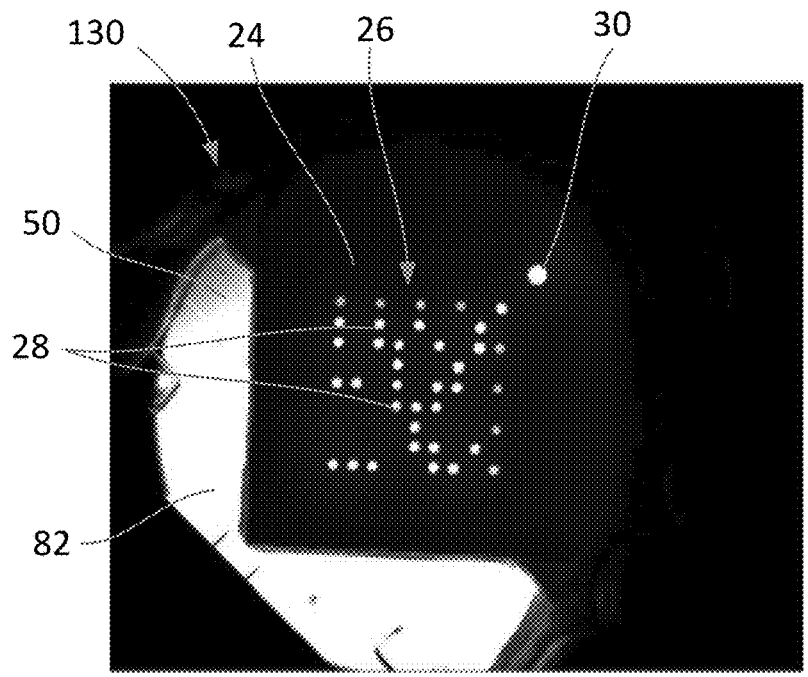
FIG. 8A illustrates an image formed by the through hole pattern of the data match code.
Figure 8B:
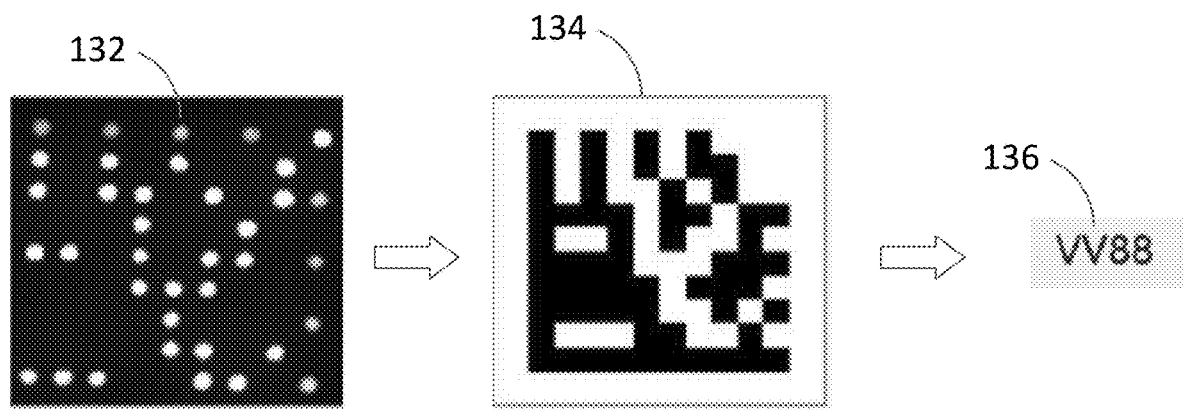
FIG. 8B illustrates how the imaged data match coding may be converted to an alphanumeric value.

FIG. 8A illustrates the patterned image 130 formed by the through-holes 28 of the data match code 26 when the back light transmitted from the light source 98 is transmitted through the platform 26. A portion of the assembly 50 may be seen located upon the positioning plate 82 and the back light transmitted through the through-holes 28 of the data match code 26 may be seen in relation to the reference hole 30. FIG. 8B illustrates how the imaged data match coding 132 as received from the imager 84 may be recognized by the processor so that the imaged data match coding 132 with gray-value image features may reconstruct the data match codes with gray-value image features. Hence, the imaged data match coding 132 may be converted into a black-and-white image 134 forming a composite, digitized image where the light transmitted through a through-hole 28 is converted into a white-colored square and spaces or locations between or adjacent to the through-hole 28 where the light is blocked is converted into a black-colored square. The resulting black-and-white image 134, as shown, may correspond to a digitized version corresponding to the imaged data match coding 132.

The black-and-white image 134 may then be processed by the processor 100 for conversion into a recognized alphanumeric value such as the data match value 136 shown. Multiple data match codes from different orthodontic appliances may be imaged sequentially by the imaging system 80 and the images may be stored in a memory component and sent to the processor 100 for analysis and processing.

While different features are discussed, the system may incorporate any number of different features into a single system in any number of combinations. A single system provided may, for example, include or incorporate every feature described herein or it may include a select number of features depending upon the desired system.

The applications of the devices and methods discussed above are not limited to the one described but may include any number of further treatment applications. Modification of the above-described assemblies and methods for carrying out the invention, combinations between different variations as practicable, and variations of aspects of the invention that are obvious to those of skill in the art are intended to be within the scope of the claims.

What is claimed is:

1. A data match code apparatus, comprising:
   a three-dimensional model corresponding to a patient dentition; and
   a platform extending from the three-dimensional model, wherein the platform defines a data match code having a plurality of through-holes which are positioned relative to one another in a predetermined pattern.

2. The apparatus of claim 1 wherein the platform is formed integrally with the three-dimensional model.

3. The apparatus of claim 1 wherein the three-dimensional model defines one or more positioning splines along a surface of the model.

4. The apparatus of claim 1 wherein the platform further defines a reference hole located adjacent to the data match code.

5. The apparatus of claim 1 wherein the plurality of through-holes extend through a thickness of the platform.

6. The apparatus of claim 1 further comprising a film or membrane formed upon the three-dimensional model and the platform such that the data match code is visible through the film or membrane.

7. The apparatus of claim 1 further comprising an imager configured to be in alignment with the data match code such that the imager receives an image of the predetermined pattern when a light is transmitted through the through-holes from a bottom or top surface of the platform.

8. The apparatus of claim 7 further comprising a processor in communication with the imager, wherein the processor is configured to receive the image of the predetermined pattern and convert the image into a black-and-white image which corresponds to the predetermined pattern.

9. The apparatus of claim 8 wherein the processor is configured to further convert the black-and-white image into an alphanumeric code.

10. A data match code apparatus, comprising:
    a three-dimensional model corresponding to a patient dentition;
    a platform extending from the three-dimensional model, wherein the platform defines a data match code having a plurality of through-holes which are positioned relative to one another in a predetermined pattern;
    a film or membrane formed upon the three-dimensional model and the platform such that the data match code is visible through the film or membrane; and
    an imager configured to be in alignment with the data match code such that the imager receives an image of the predetermined pattern when a light is transmitted through the through-holes from a bottom or top surface of the platform.

11. A method of coding an oral appliance, comprising:
    exposing a light upon a bottom or top surface of a platform which defines a data match code having a plurality of through-holes which are positioned relative to one another in a predetermined pattern, where the platform extends from a three-dimensional model which corresponds to a patient dentition;
    receiving an image upon an imager in communication with a processor, where the image is formed by a portion of the light transmitted through the plurality of through-holes to form the image which corresponds to the predetermined pattern;
    converting via the processor the image to a composite image; and
    converting via the processor the composite image to an alphanumeric value which corresponds to a unique identifier associated with the oral appliance.

12. The method of claim 11 wherein the image is formed by the portion of the light transmitted through the plurality of through-holes and a film or membrane placed upon the platform and the three-dimensional model.

13. The method of claim 11 wherein exposing the light comprises transmitting the light through a diffuser positioned proximal to the bottom or top surface of the platform.

14. The method of claim 11 wherein receiving the image comprises receiving the image via a CMOS camera.

15. The method of claim 11 wherein converting via the processor the image comprises converting a gray-value image to the composite image.

16. The method of claim 15 wherein converting the gray-value image comprises converting the gray-value image to a black-and-white image.

17. The method of claim 11 further comprising processing the oral appliance based on the alphanumeric value.

* * * * *